(12) United States Patent
Landry et al.

(10) Patent No.: US 10,401,605 B2
(45) Date of Patent: Sep. 3, 2019

(54) STRUCTURED ILLUMINATION IN INVERTED LIGHT SHEET MICROSCOPY

(71) Applicants: SCREEN HOLDINGS CO., LTD., Kyoto-shi, Kyoto (JP); The Board of Trustees of the Leland Stanford Junior University, Stanford, CA (US)

(72) Inventors: Joseph Russell Landry, Stanford, CA (US); Ryosuke Itoh, Stanford, CA (US); Michael J. Mandella, Palo Alto, CA (US); Olav Solgaard, Stanford, CA (US)

(73) Assignees: SCREEN HOLDINGS, CO., LTD., Kyoto (JP); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 15/843,692

(22) Filed: Dec. 15, 2017

(65) Prior Publication Data
US 2018/0321479 A1    Nov. 8, 2018

Related U.S. Application Data

(60) Provisional application No. 62/500,359, filed on May 2, 2017.

(51) Int. Cl.
*G02B 21/00* (2006.01)
*G01N 21/64* (2006.01)
*G02B 21/36* (2006.01)

(52) U.S. Cl.
CPC ..... *G02B 21/0088* (2013.01); *G01N 21/6458* (2013.01); *G02B 21/0032* (2013.01);
(Continued)

(58) Field of Classification Search
CPC ............ G02B 21/0088; G02B 21/0032; G02B 21/0076; G02B 21/365; G01N 21/6458
See application file for complete search history.

(56) References Cited

U.S. PATENT DOCUMENTS

| 2013/0286181 A1* | 10/2013 | Betzig .................... H04N 7/18 348/79 |
| 2014/0340483 A1* | 11/2014 | Ritter ................. G01N 21/6458 348/46 |

(Continued)

OTHER PUBLICATIONS

A. Glaser and J.T. Liu, "A light sheet microscopy system for rapid, volumetric imaging and pathology of large tissue specimens", in Biomedical Optics 2016, OSA Technical Digest (online) (Optical Society of America, 2016), paper CTh1A.4.

*Primary Examiner* — Michael C Bryant
(74) *Attorney, Agent, or Firm* — McDermott Will & Emery LLP

(57) ABSTRACT

A system, including a structured illumination stage to provide a spatially modulated imaging field is provided. The system further includes a spatial frequency modulation stage to adjust the frequency of the spatially modulated imaging field, a sample interface stage to direct the spatially modulated imaging field to a sample, and a sensor configured to receive a plurality of fluorescence emission signals from the sample. The system also includes a processor configured to reduce a sample scattering signal and to provide a fluorescence emission signal from a portion of the sample including the spatially modulated imaging field. A method for using the above system to form an image of the sample is also provided.

10 Claims, 12 Drawing Sheets

(52) U.S. Cl.
CPC ....... *G02B 21/0076* (2013.01); *G02B 21/365* (2013.01); *G02B 21/367* (2013.01); *G01N 2201/0675* (2013.01)

(56) References Cited

U.S. PATENT DOCUMENTS

| | | | |
|---|---|---|---|
| 2015/0362713 A1* | 12/2015 | Betzig | G02B 21/0064 250/459.1 |
| 2016/0041099 A1* | 2/2016 | Parthasarathy | G01N 21/6458 250/459.1 |
| 2016/0062098 A1* | 3/2016 | Brown | G02B 21/0076 348/80 |
| 2017/0357084 A1* | 12/2017 | Park | G01N 21/4133 |

\* cited by examiner

STRUCTURED ILLUMINATION IN INVERTED LIGHT SHEET MICROSCOPY

CROSS-REFERENCE TO RELATED APPLICATIONS

The present disclosure is related and claims priority to U.S. Provisional Patent Application No. 62/500,359, entitled STRUCTURED ILLUMINATION IN INVERTED LIGHT SHEET MICROSCOPY, by Joseph Landry, et-al. filed on May 2, 2017, the contents of which are hereby incorporated by reference in their entirety, for all purposes.

STATEMENT REGARDING US GOVERNMENT SPONSORED RESEARCH

Some of the disclosure of the present application were developed using U.S. government grant NIH 5R01CA 180152-02. The U.S. government may have some interest in the present application.

TECHNICAL FIELD

Embodiments described herein are generally related to the field of microscopy imaging of tissue. More specifically, embodiments described herein are related to high resolution fluorescence imaging of tissue.

BACKGROUND

Imaging of deep tissue using fluorescence microscopy presents challenges stemming from the high scattering induced by dense tissue, which typically obfuscates fluorescence signals. Confocal fluorescence techniques have been successful to reduce scattering interference in the imaging signal, but at the cost of signal intensity, therefore limiting the quality of the image that can be obtained during a limited collection time. Adding to scattering interference effects, microscopy approaches address a reduced field of view (FOV) resulting from the high numerical apertures (NA) typically used in high magnification systems, which result in large aberrations at the edge of the images in the focal plane of the objective. The lateral aberrations result in reduced spatial resolution, which is typically compensated by convolved scanning mechanisms involving moving parts and increasing image collection times.

The description provided in the background section should not be assumed to be prior art merely because it is mentioned in or associated with the background section. The background section may include information that describes one or more aspects of the subject technology.

SUMMARY

In a first embodiment, a system includes a structured illumination stage to provide a spatially modulated imaging field, a spatial frequency modulation stage to adjust the frequency of the spatially modulated imaging field, and a sample interface stage to direct the spatially modulated imaging field to a sample. Further, the system includes a sensor configured to receive a plurality of fluorescence emission signals from the sample and a processor configured to reduce a sample scattering signal and to provide a fluorescence emission signal from a portion of the sample including the spatially modulated imaging field.

In a second embodiment, a system includes a first optical element configured to spatially separate two optical beams, and a second optical element configured to spatially combine the two optical beams. The second optical element further includes a focusing element and a linearly movable reflector configured to direct a first and a second of the two optical beams to a first and a second points of the focusing element, wherein the first and second points of the focusing element are disposed axially symmetric relative to one another about a symmetry axis of the focusing element.

In a third embodiment, a sample interface for inverted fluorescence microscopy includes a wavefront matching optic having a center of curvature beyond a plane forming a flat side of the wavefront matching optic, and a sample cover glass disposed adjacent to the flat side of the wavefront matching optic. The sample interface also includes an illumination objective configured to form an illumination field on a sample by directing two optical beams through the wavefront matching optic, the two optical beams forming an incident plane at an incident angle relative to the sample cover glass, and a microscope objective configured to collect a fluorescent signal excited in the sample by the illumination field along a direction perpendicular to the incident plane. The incident angle is one of approximately 60° or approximately 30°, an optical axis of the illumination objective intersects an optical axis of the microscope objective at the center of curvature of the wavefront matching optic, and the illumination field includes a structured illumination field having a spatial frequency on the incident plane.

In yet another embodiment, a method for forming an image of a sample includes providing a spatially modulated imaging field and adjusting a frequency of the spatially modulated imaging field. The method further includes directing, with a sample interface, the spatially modulated imaging field to a sample, receiving a plurality of fluorescence emission signals from the sample, and combining the plurality of fluorescence emission signals to reduce a sample scattering signal and to obtain an image of the sample.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

Figure 1A:
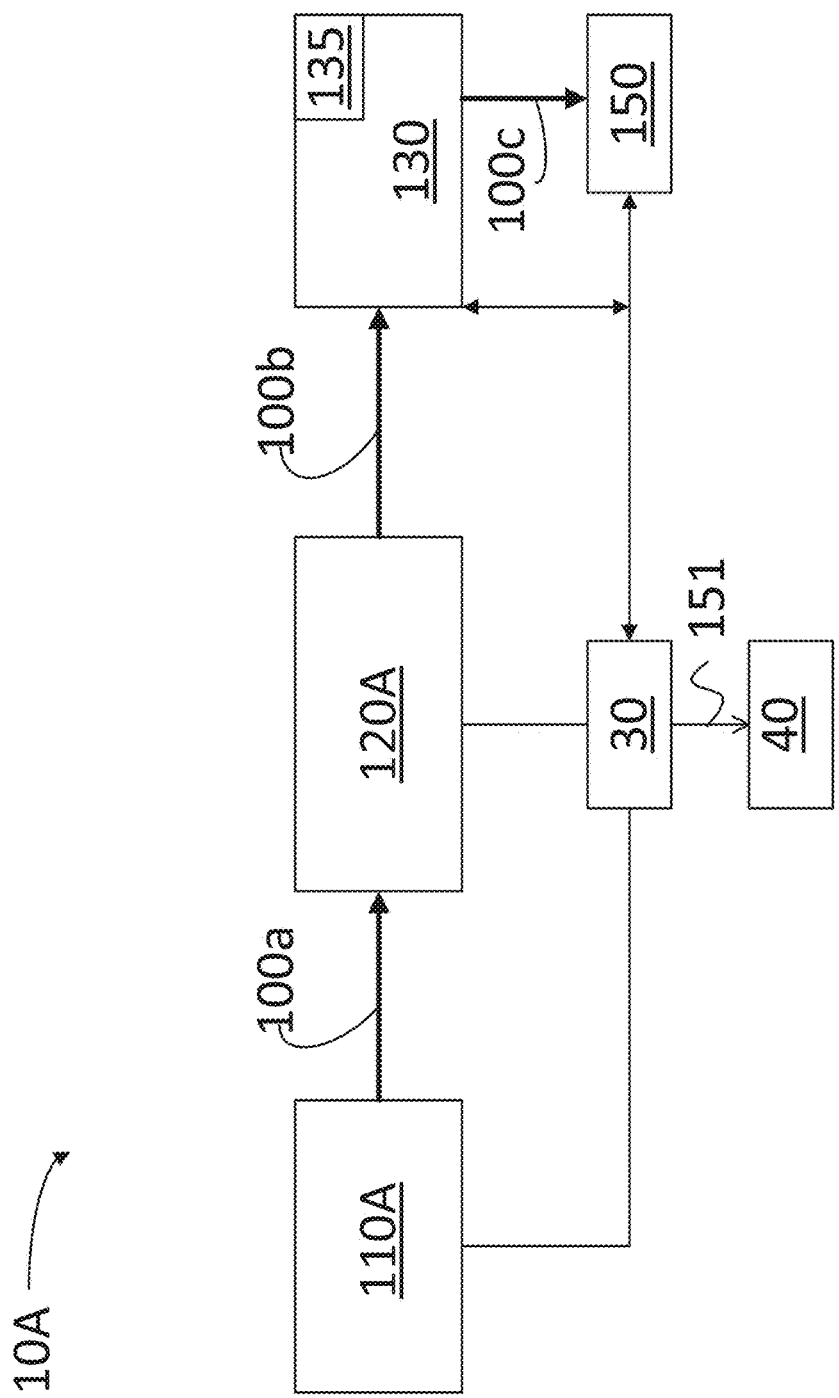
FIG. 1A illustrates a system for illuminating a sample with a structured illumination (SI) system and collecting an image from the sample, according to some embodiments.

In the figures, elements and steps denoted by the same or similar reference numerals are associated with the same or similar elements and steps, unless indicated otherwise. In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

General Overview

Embodiments as disclosed herein include an inverted light sheet fluorescence microscope using structured illumination for imaging of thick specimens. A wavefront matching optic is incorporated into the tissue interface, enabling an accessible, inverted configuration without sacrificing resolution. Production of structured illumination using a high-speed one-dimensional (1D) spatial light modulator facilitates rapid acquisition of patterned images and both out-of-focus and scattered signal removal. Embodiments as disclosed herein demonstrate improved resolution and contrast for images using fluorescent beads in animal tissue specimens.

Light sheet fluorescence microscopy (LSFM) has transformed imaging in the life sciences due to the technique's ability to rapidly acquire optical sections in thick specimens. Optical sectioning in LSFM uses lower peak intensities compared to other optical sectioning techniques, such as confocal microscopy, leading to the additional benefit of lower photo-bleaching. Together, the high speed and favorable photo-bleaching properties of LSFM make it a powerful tool for volumetric reconstructions and time-lapse imaging. In order to image in thick specimens, two features may be desirable: samples may be transparent and be conducive to the mounting constraints inherent to LSFM. Embodiments as disclosed herein may satisfy these features thereby benefiting a number of applications of LSFM. When a sample is confined to a dish or multi-well plate in confocal or wide-field microscopy, an inverted configuration may often be desirable. In some embodiments, an upright objective may be desirable to free-up space on the sample stage and to enable imaging directly through a window at the bottom of a dish. In a microscope system consistent with some embodiments disclosed herein, the microscope may be open above the horizontal plane and contain an illumination and imaging beam intersection. Some embodiments may use a flat glass window to support the sample, which may be replaced with glass-bottom dishes or multi-well plates.

Some embodiments may mitigate aberrations and decreased resolution due to obliquely imaging across a flat glass window by judiciously choosing the imaging configuration. For example, in some embodiments reduced aberrations may be obtained by inserting a "water prism," cylindrical lenses, and deformable mirrors. Some embodiments may reduce the optical complexity of the imaging configuration by including a single, vertical objective.

FIG. 1A illustrates a system 10A for illuminating a sample 135 with a spatially modulated imaging field 100a and collecting an image from the sample, according to some embodiments. A structured illumination (SI) stage 110A is configured to provide the spatially modulated imaging field 100a. A spatial frequency modulation stage 120A is configured to adjust a frequency of the spatially modulated imaging field 100a and form spatially modulated imaging field 100b with an adjusted spatial frequency. System 10A may also include a sample interface stage 130 to direct spatially modulated imaging field 100b to sample 135. A sensor 150 configured to receive a plurality of fluorescence emission signals 100c from sample 135. Without limitation, sensor 150 may include a 2D array of sensing pixels (e.g., as in a CMOS camera—sCMOS and the like- or a CCD camera). In some embodiments, sensor 150 may capture oblique sections of the sample, which are used to reconstruct a final image (e.g., a 3D image).

In some embodiments, spatial frequency modulation stage 120A includes a reduced number of diffractive elements (e.g., gratings, diffraction prisms and the like). This feature is particularly desirable in embodiments where multiple illumination wavelengths are desirable. Further, some embodiments of system 10A may be configured to operate in the near infra-red (NIR) wavelength region (e.g., from about 750 nm to about 2500 nm), since this is a spectral region that renders lower light scattering from tissue samples. Accordingly, stages 110A and 120A may be configured to operate in the NIR region at a high speed, for multiple illumination wavelengths without having to reconfigure the system.

Fluorescence emission signals 100c are generated by the light intensity patterns in spatially modulated imaging field 100b. At least one processor 30 is programmed by a program that may be stored in a memory 40 to determine a noise-free fluorescence emission signal 100c from a portion of sample 135 including spatially modulated imaging field 100b. Processor 30 is configured to reduce a sample scattering signal by combining one or more of the fluorescence emission signals obtained from suitably selected spatially modulated imaging fields. In some embodiments, processor 30 generates a sample image 151 that is stored in memory 40.

Figure 1B:
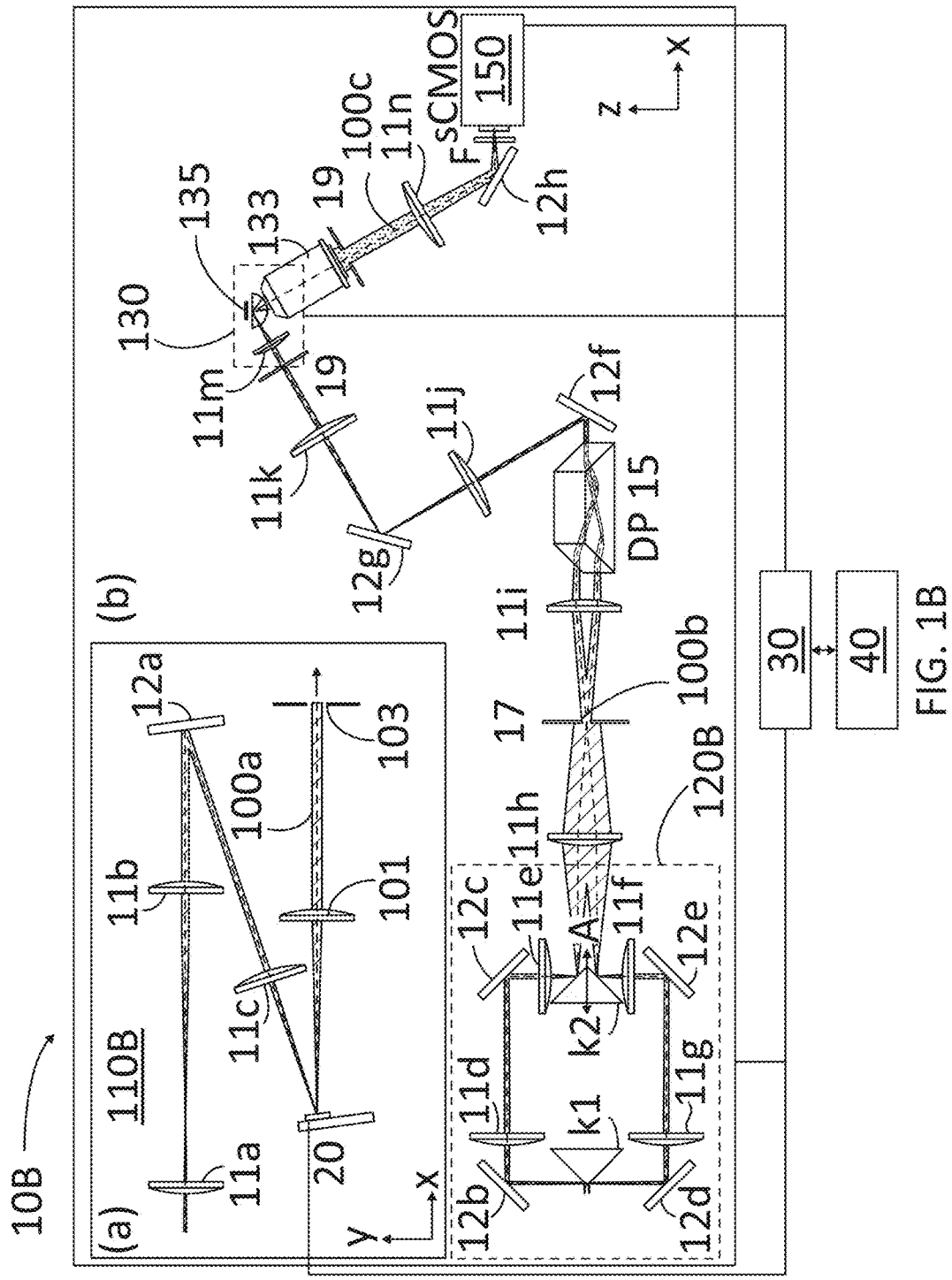
FIG. 1B illustrates a system for inverted light sheet microscopy including an SI system, according to some embodiments.

FIG. 1B illustrates a system 10B for inverted light sheet microscopy including structured illumination (SI) stage 110B, according to some embodiments. System 10B shows detailed components that may implement blocks shown in FIG. 1A. Without limitation, the illumination beam may include a single beam including two wavelengths, 660 nm and 785 nm. Lenses 11a and 11b expand the illumination beam. A lens 11c focuses the illumination beam onto SI stage 110B (which is, e.g., SI stage 110A in FIG. 1A) including a spatial light modulator (SLM) 20 configured to spatially separate two diffracted beams having a selected phase shift between them, to form the spatially modulated imaging field. Lens 11c may be an achromatic cylindrical lens. SLM 20 in embodiments consistent with the present disclosure is a device that forms a spatially structured pattern, which when interacting with a light beam, forms a pre-determined reflected, refracted, or diffracted beam based on interference patterns in specific propagation directions, arising from the spatially structured pattern. In some embodiments, SLM 20 may include a grating light-valve (GLV) or a liquid crystal on silicon (LCoS). In some embodiments, SLM 20 is adapted as, but not limited to, a special light modulator, in consideration of process speed. An example of the SLM 20 is discussed in more detail below. In some embodiments, SI stage 110B generates multiple diffracted orders that pass through lens 101 to a double-slit 103, which allows the first order beams (e.g., +1 and −1 diffraction orders) to proceed to sample illumination. In a spatial frequency modulation stage 120B (which is, e.g., spatial frequency modulation stage 120A in FIG. 1A), the +1 and −1 diffracted beams are separated by a first prism k1. Further, spatial frequency modulation stage 120B may include mirrors 12b, 12c, 12d, and 12e to reduce or adjust the size of each of the diffracted beams selected in slit 103. The diffracted beams may be imaged onto a second prism k2, and pass through a relay optics including lenses 11h and 11i.

In some embodiments, SI stage 110B is configured to generate two illumination beams that are coherent and have a selected phase retardation between one another. SLM 20 is configured to generate two diffraction beams from the incoming illumination beam corresponding to a +1 and a −1 diffraction order, and further to apply a selected phase shift between the +1 and the −1 diffraction beams. In some embodiments system 10B may block the zeroth order of diffraction, in case this is a propagating mode. In some embodiments, the zeroth order of diffraction may include specular reflection or in-phase modulation, which system 10B may use for image collection (e.g., as a reference or calibration beam). In some embodiments, double slit 103 separates the optical paths of the +1 and the −1 diffraction beams from SLM 20. In some embodiments, SLM 20 may include a 1-D spatial light modulator that manipulates the phase of an incoming wave front with movable ribbons capable of switching at hundreds of kHz. Further, in some embodiments, SLM 20 supports multiple wavelengths simultaneously. Accordingly, in some embodiments, it is possible to shift two disparate patterns in a structured illumination configuration, with each pattern operating at a different illumination wavelength. Further, SLM 20 may provide an extended displacement for the movable ribbons (e.g., a maximum required displacement of each of a GLV ribbon of $\lambda/4$ for long wavelengths in the red and NIR spectra while maintaining a high operation speed. In some embodiments, a GLV may provide a displacement of each GLV ribbon by an amount approximately equal to $2\lambda/3$. The extent of the displacement provided to each GLV ribbon may vary according to the application and other specifications of the optical components used. Accordingly, in some embodiments it may be desirable to use longer illumination wavelengths due to lower scattering effects in dense tissues, compared to blue and green light.

Spatial frequency modulation stage 120B is configured to adjust a spatial frequency of an interference pattern between the +1 and the −1 diffraction beams from double slit 103. Stage 120B may include knife edge prisms k1 and k2, of which at least one may be movable along an axis A (see FIG. 2B). Accordingly, in some embodiments a linear displacement of one of prisms k1 or k2 along the axis may determine the spatial frequency of the interference pattern between the +1 and the −1 diffraction beams.

System 10B may also include a field stop (FS) 17 to select a portion of an interference pattern formed by the +1 and the −1 diffraction beams after stage 120. In some embodiments, FS 17 may reduce undesirable scattering effects from portions of the illumination beam that are outside the region of interest in the sample. Further, in some embodiments a dove prism (DP) 15 rotates the interference pattern about an optical axis of the illumination system to deliver an illumination field onto the sample in a sample interface (SI) 130. In some embodiments, DP 15 rotates the interference pattern by about 90° before the beam reaches mirror 12f, which is conjugate to lens 11m into the sample interface 130. In some embodiments, the optical train formed by mirrors 12f-12g and lenses 11j, 11k, and 11m, including at least one or two, or more, aperture stop (AS) 19 is configured to provide an illumination field at about 60° from vertical relative to sample interface 130.

Sample interface 130 may include a detection objective (DO) 133 to collect an image formed by imaging field 100b on sample 135. In some embodiments, the image is formed by a fluorescent signal induced by imaging field 100b on the sample and collected by DO 133. In some embodiments, sample interface 130 may include a tube lens (TL) and a filter F, before relaying the image to sensor 150. Filter F may be a band-pass filter (660 nm), or a long-pass filter (785 nm) configured to block or suppress the illumination wavelength, and to allow passage of the fluorescent emitted light from the sample into the sensor.

In some embodiments, system 10B includes memory 40 communicatively coupled with processor 30. Memory 40 may include any type of non-transitory, computer readable medium storing instructions, commands, and data. Processor 30 may be configured to execute instructions stored in memory 40 which, when executed by processor 30, cause system 10B to perform a light sheet fluorescence microscopy (LSFM) image collection. Accordingly, processor 30 may be configured to control the SLM in phase shifting stage 110B, or at least one of the knife edge prisms k1 and k2 in spatial frequency modulation stage 120B. Processor 30 may also be configured to control sample interface 130. Further, processor 30 may be configured to cause sensor 150 to collect an image. Moreover, processor 30 may receive the image from the sensor and process the image accordingly, e.g., storing a processed image in memory 40. Processor 30 may be implemented by circuitry including, but not limited to, at least one semiconductor integrated circuit such as at least one processor (e.g., a central processing unit (CPU)), at least one application specific integrated circuit (ASIC), and/or at least one field programmable gate array (FPGA). Memory 40 may take many forms, including, but not limited to, any type of magnetic medium such as a hard disk, any type of optical medium such as a CD and a DVD, any type of semiconductor memory such as a volatile memory and a non-volatile memory. The volatile memory may include a DRAM and a SRAM, and the nonvolatile memory may include a ROM and a NVRAM. The semiconductor memory is also a semiconductor circuit which can be a part of the circuitry together with at least one processor. The ASIC is an integrated circuit (IC) customized to perform, and the FPGA is an integrated circuit designed to be configured after manufacturing in order to perform, all or a part of the functions of the elements shown in FIG. 1B.

Hereinafter, and for notation simplicity, lenses 11a through 11n will be collectively referred to as "lenses 11." Likewise, mirrors 12a through 12h will be collectively referred to as "mirrors 12." In some embodiments, lenses 11 may include achromatic spherical lenses, aspherical lenses, anamorphic lenses, or any combination of the above. Mirrors 12 may include planar mirrors, spherical mirrors, concave mirrors, convex mirrors, or any combination of the above. Further, in some embodiments, at least one of the moving components in system 10B may be manually actuated by an operator. Hereinafter, systems 10A and 10B will be referred to as "system 10." Likewise, SI stages 110A and 110B will be referred to, hereinafter, as SI stage 110. Furthermore, spatial frequency modulation stages 120A and 120B will be referred to, hereinafter, as spatial frequency modulation stage 120. System 10 uses SI stage 110 and spatial frequency modulation stage 120 to reduce the effect of scattered and out-of-focus fluorescence, thereby substantially improving image quality.

Figure 2A:
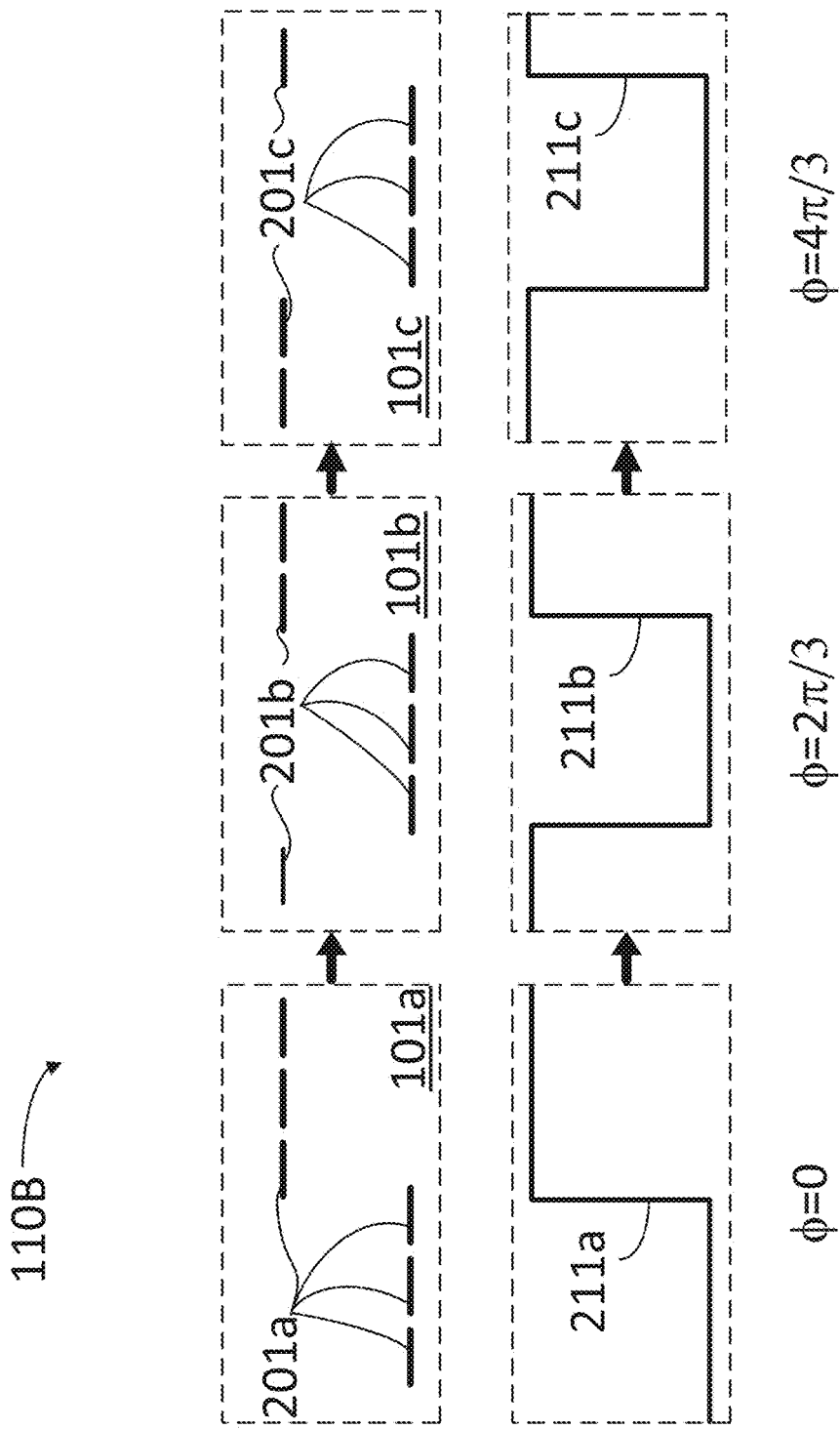
FIG. 2A illustrates an optical configuration to adjust a spatial phase for an SI system, according to some embodiments.
Figure 2B:
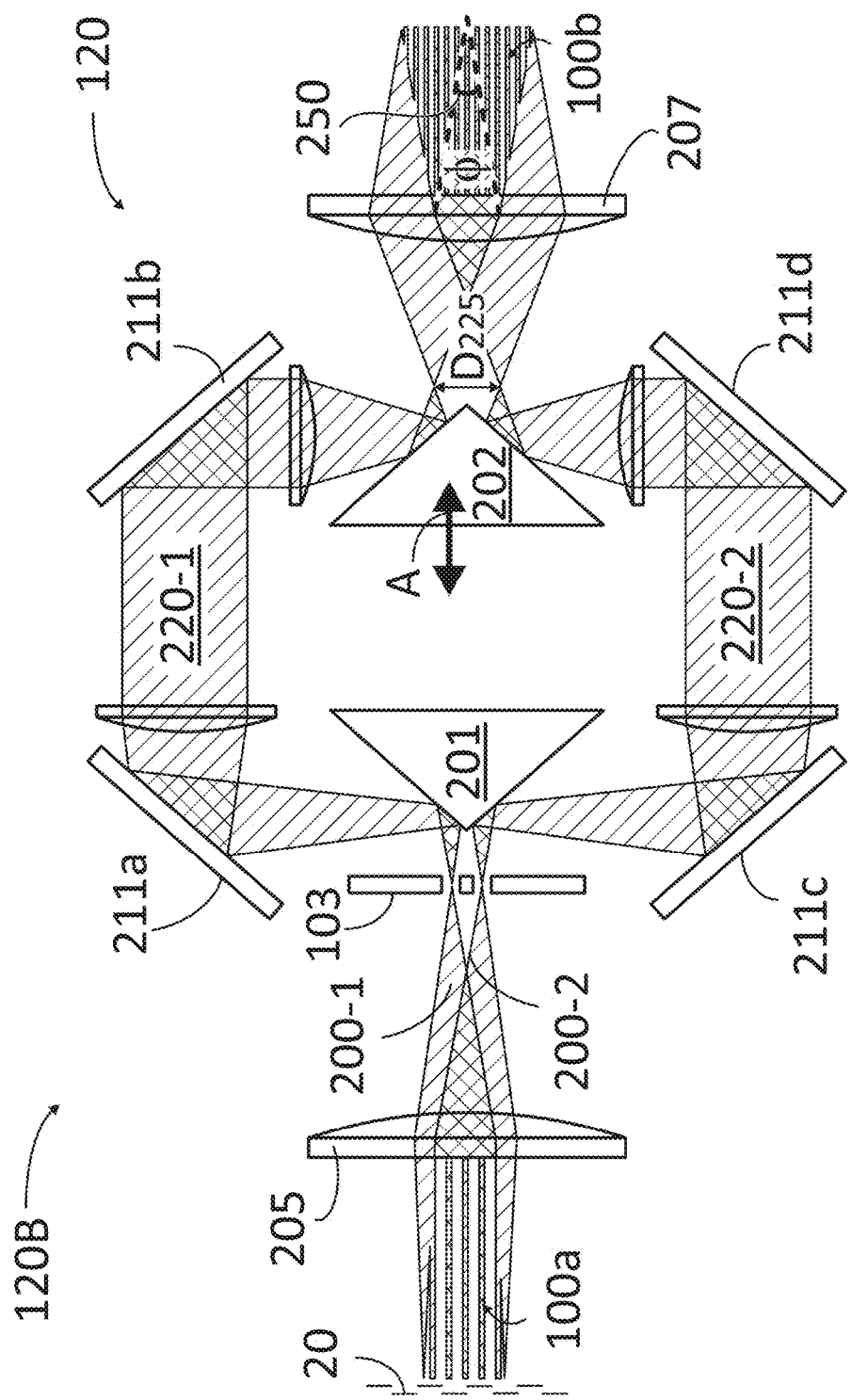
FIG. 2B illustrates an optical configuration to adjust a spatial frequency in an SI system, according to some embodiments.

FIG. 2A illustrates SI stage 110B, configured to adjust a spatial phase, p, for SI system 10B, according to some embodiments. Three SLM pixel configurations, 201a, 201b, and 201c, corresponding to three square wave phase states 211a, 211b, and 211c, respectively (e.g., φ=0, φ=2π/3, φ=4π/3) are assigned to SLM 20. For each state, these orders produce a sinusoidal field profile at the image plane with both a fixed spatial frequency determined by the configuration of spatial frequency modulation stage 120B, and a phase, φ, determined by the configuration of SLM 20. In some embodiments, adjustment of the spatial frequency may be achieved by translating second prism k2, in spatial frequency modulation stage 120B, which directly affects the beam separation. In some embodiments, the translation of second prism k2 may be performed manually, by an operator. To change the phase, φ, a periodic template of 3 "off" and 3 "on" pixels in the SLM of stage 110B that defines each state is shifted by a single pixel from one state to the next (see arrows in FIG. 2B showing the phase changes). "On" pixels are set to have displacements of λ/4 relative to the "off" pixels for maximum first order diffraction efficiency. As a whole, this configuration generates three frequency-adjustable SI intensity patterns with phases 0, 2π/3, and 4π/3.

FIG. 2B illustrates spatial frequency modulation stage 120B, configured to adjust a spatial frequency in SI system 10B using spatial frequency modulation stage 120, according to some embodiments. Incoming beams 200-1 and 200-2 (collectively referred to, hereinafter, as "beams 200") are separated by prism 201 into a path 220-1 over mirrors 211a and 211b, and a path 220-2 over mirrors 211c and 211d. Eventually, the beams come together at an angle, φ 250, after reflecting off prism 202 and going through lens 207. Sinusoidal interference patterns 100a and 100b between beams 200-1 and 200-2 are generated by spatially overlapping two light sheets formed by incoming beams 200. Note that the spatial frequency of patterns 100a and 100b need not be the same. Angle φ 250 results from the separation D 225 between beams 200 as they impinge symmetrically about the axis of lens 207. In some embodiments prism 202 is movable, manually by an operator or automatically by processor 30, about the optical axis of spatial frequency modulation stage 120B, which in turn adjusts D 225 thereby modifying the period of the spatial modulation. Accordingly, a larger D 225, the larger angle φ 250 will result, thereby decreasing the spatial period (e.g., increasing the spatial frequency) of modulated imaging field 100b. A desirable feature of spatial frequency modulation stage 120B is that the frequency modulation obtained may be adjusted simply by selecting the displacement of prism 202 accordingly without limitations of the wavelength of beam 200. Thus, SI system 10B may be configured to operate with multiple illumination wavelengths.

With the three phase-shifted patterns 100b resulting from SI stage 110B and spatial frequency modulation stage 120B, three images $I_1$, $I_2$ and $I_3$ may be collected (each corresponding to a structured illumination (SI) pattern including imaging field 100b, having the same frequency and a different phase, φ), and a sample image $I_{SI}$ may be reconstructed according to $$I_{SI} = \sqrt{(I_1-I_2)^2 + (I_2-I_3)^2 + (I_3-I_1)^2} \quad (1)$$

In embodiments as disclosed herein, an imaging with structured illumination ($I_{SI}$) scheme uses Eq. 1 to eliminate scattered light contributions to $I_1$, $I_2$, and $I_3$, which largely remains the same, regardless of SI pattern (which is, e.g., modulated imaging field 100b). Furthermore, Eq. 1 can remove out-of-focus background. If the light sheet thickness is greater than the objective depth-of-field then, for sufficiently high spatial frequency if imaging field 100b, the pattern will be blurred by a modulation transfer function (MTF) of the objective above and below the sample plane, resulting in subtraction of those background contributions. In contrast to image $I_{SI}$, a conventional image may be simply a sum image, $I_{sum}$, defined as $I_{sum}=I_1+I_2+I_3$.

As the sample is scanned through each pixel in the sensor, the three images ($I_1$, $I_2$, and $I_3$) are collected corresponding to each state of the SLM. Using Eq. 1, an oblique SI image is reconstructed (e.g., $I_{SI}$). Due to the obliquely captured images, each horizontal line in the reconstruction is mapped to a specific tissue depth. The mapping and the sample scan along the horizontal (XY) plane enable two imaging modes: a 3D volume reconstruction by stacking 2D oblique sections, and rapid 2D XY sections by lining up sequences of reconstructed lines.

Figure 3A:
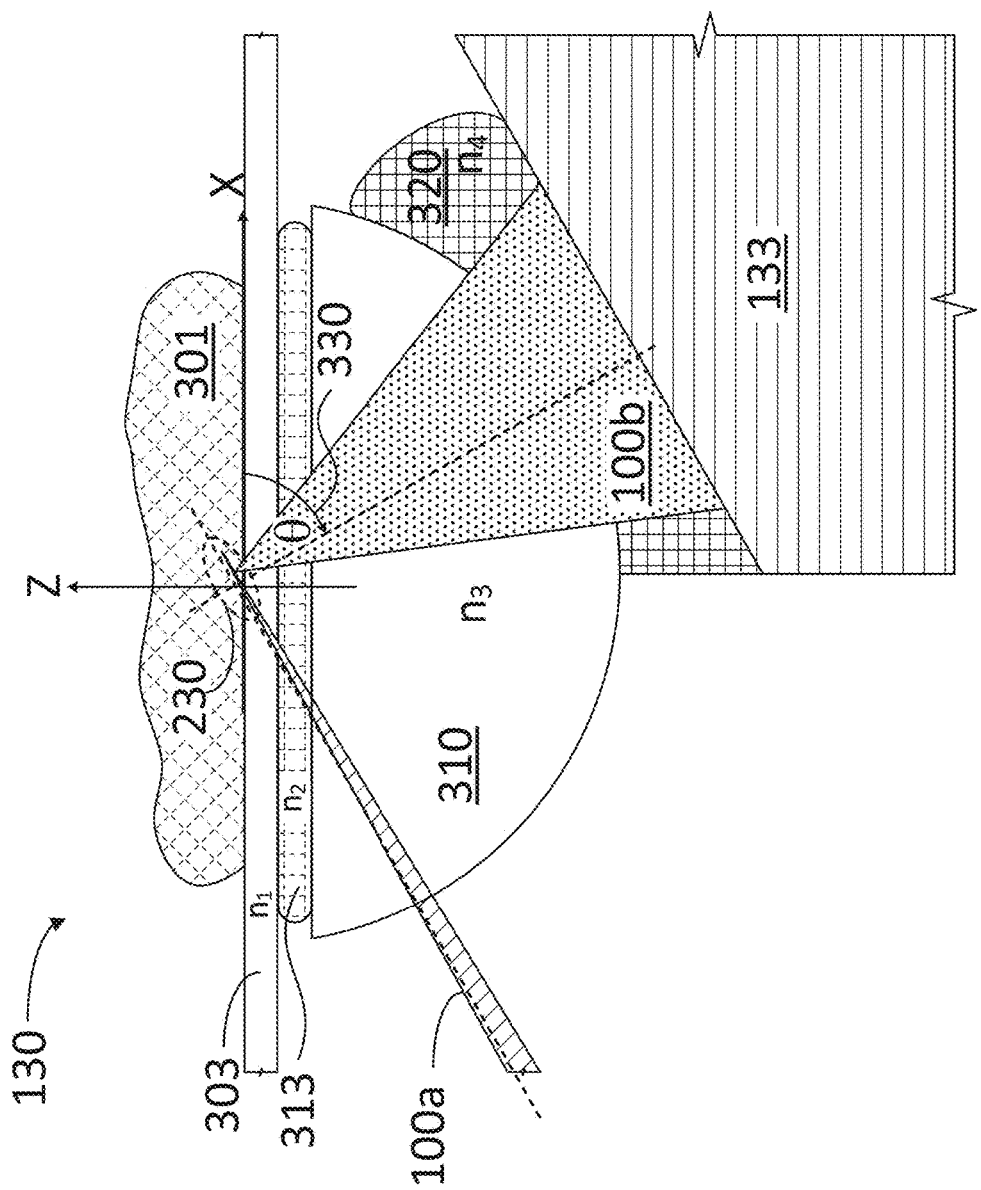
FIG. 3A illustrates a sample interface configuration in an SI system, according to some embodiments.

FIG. 3A illustrates sample interface 130 in a system 10, according to some embodiments. DO 133 may be stopped down to a numerical aperture (NA) of 0.48, which slightly oversamples the object for emission spectra arising from 660 nm and 785 nm excitable fluorophores. In object space, the expected Rayleigh resolution may be 0.82 µm for 700 nm fluorescence signal emission (illumination wavelength at 660 nm) and 0.96 µm for 820 nm fluorescence signal emission (illumination wavelength at 785 nm). When sample interface 130 provides a 17.4× magnification, the anticipated sensor sampling is 0.37 µm. In some embodiments, a ray-optics simulation software provides an optimized configuration for sample interface configuration 130 for a selected NA. The simulation software may include computer-aided-design (CAD) simulations of the elements shown in FIG. 3A, assuming that the detection objective is an ideal lens, thus isolating the effect of sample interface configuration 130.

Sample interface 130 may include a mechanical element, which may be controlled by processor 30, to move sample 301 along a desired direction (e.g., X or Y directions), for image scanning. In some embodiments, a mechanical actuator under processor 30's control may adjust a relative angle (θ) 330 between sample interface 130 and the sample stage (e.g., to adjust the imaging configuration to form a 60°-30° configuration relative to the XZ axes).

To reduce aberrations associated with oblique imaging across the glass window, in some embodiments, sample interface 130 includes a wavefront matching optic (WMO) to collect fluorescence emission from the sample and direct it to DO 133. A WMO, as disclosed herein, may include a center-reduced hemispherical lens 310, a transparent window 303 (index n1), a matching-index immersion fluid 313 (index n2). In some embodiments, transparent window 303 includes a fused silica sample window, and immersion fluid 313 may include glycerol. The WMO acts as an interface for beams to travel between different indices of refraction, unperturbed. In sample interface configuration 130, the WMO is incorporated with the center of curvature at the intersection of the illumination and detection optical axes as shown. The collection path from sample 301 (refraction index, nt), to DO 133 includes transparent window 303, index matching fluid 313, fused silica in lens 310 (n3), and water 320 (refraction index, n4). Refractive indices n1-n3 are in the range 1.458-1.472 to roughly match with the expected bulk tissue refractive indices of kidney, liver, intestine, muscle, and white matter, which range from 1.431-1.467. The index matching also shifts the focus of aberrations from transparent window 303 to the WMO-water interface. In some embodiments, sample interface configuration 130 may also include a center-reduced, hemispherical solid immersion lens (SIL) to collect the fluorescence emission from the sample and direct it to the DO.

Multiple optical rays arising from the center field point of the sample plane may be normal to the surface of the WMO that faces the sample, making the center field point aberration-free and preserving the collection half-angle. Field points off-axis may include minimal aberration, as rays refract at the WMO-water interface with small angles between relatively close refractive indices. A consequence of maintaining the collection half-angle is that the resolution and magnification are increased by a factor of $(n_3/n_4)$, with $n_3$ and $n_4$ referring to the index of refraction of the WMO and the objective immersion, respectively.

Figure 3B:
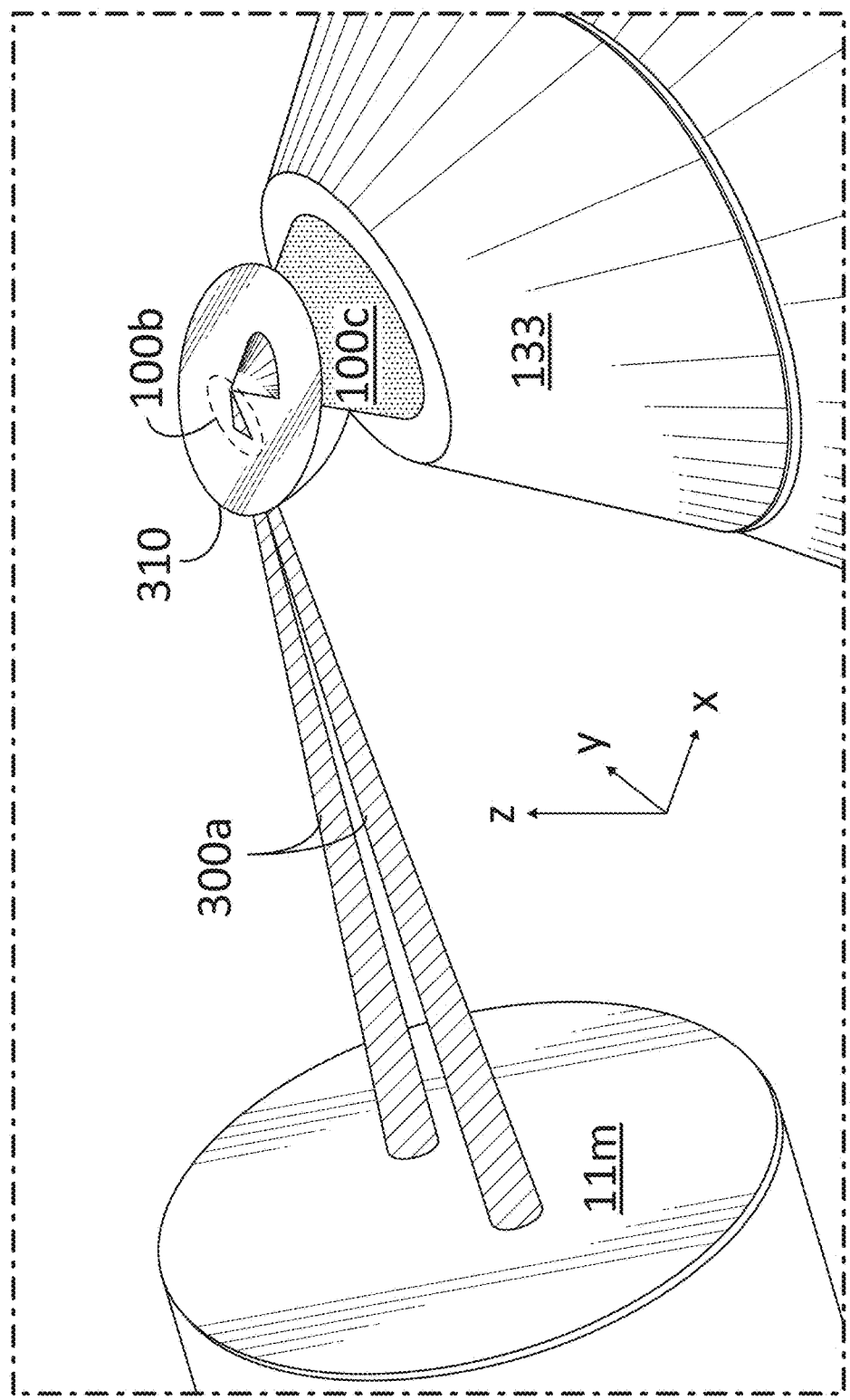
FIG. 3B illustrates a perspective view of a sample interface in a system for inverted light sheet microscopy, according to some embodiments.

FIG. 3B illustrates a perspective view of sample interface 130 in system 10, according to some embodiments. Incident beams 300a directed by lens 11m form modulated imaging field 100b in sample 135 (not shown for simplicity), through lens 310. Scattered light 100c (from sample 135) is collected by DO 133 through lens 310. Note that, in some embodiments, the angle formed by incident beams 300a and scattered light 100c collected by DO 133 is approximately a right angle (e.g., 90°). Moreover, imaging field 100b and the apex of the collection cone for scattered light 100b form a focal area located a few microns outside of the planar side of lens 310.

Figure 4A:
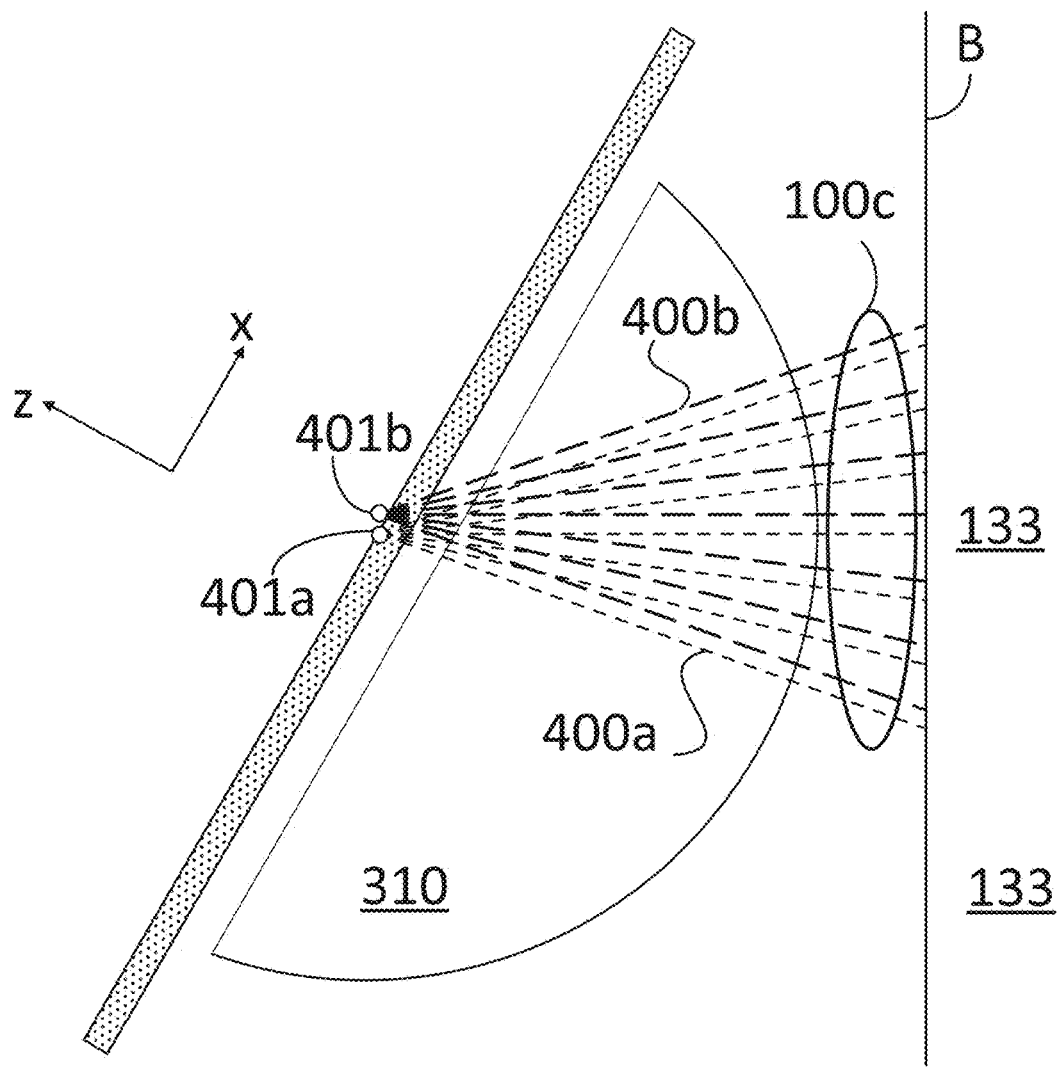
FIG. 4A illustrates a cross section view of a sample interface configuration for an SI system, according to some embodiments.

FIG. 4A illustrates a cross section view in sample interface 130, according to some embodiments. Two field points 401a and 401b form the focal area of lens 310. Field points 401a and 401b, which may be chosen are on the perimeter of the region that will be actively imaged for reconstruction of XY sections. Accordingly, a scattered ray cone 400a may be originated from field point 401a, and a scattered ray cone 400b may be originated from field point 401b. At least some of the beams in scattered ray cones 400a and 400b may form scattered light 100c collected by DO 133. Scattered ray cones 400a and 400b will be collectively referred to, hereinafter, as "ray cones 400").

Figure 4B:
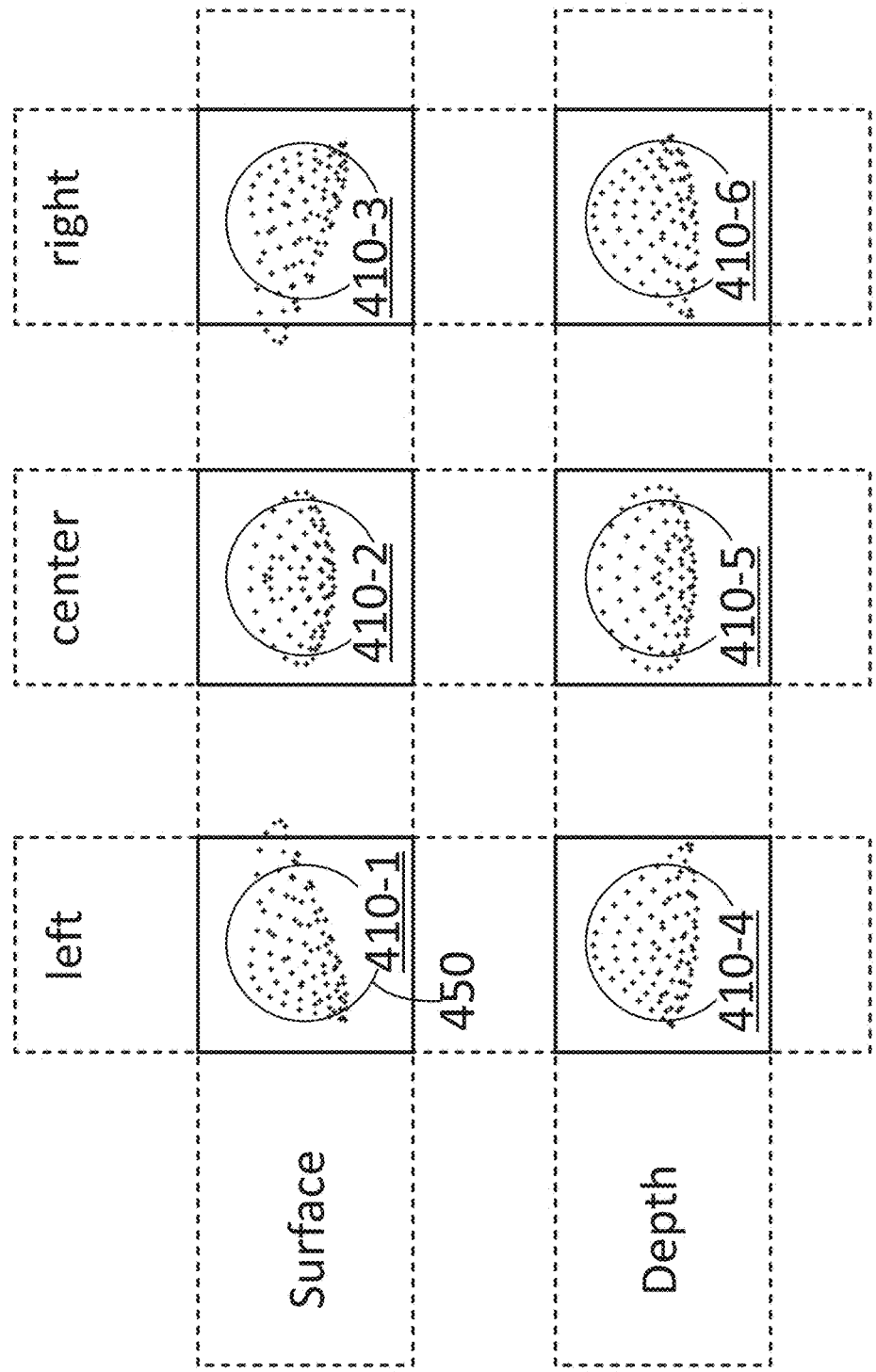
FIG. 4B illustrates spot diagrams in a sample interface configuration for an SI system, according to some embodiments.

FIG. 4B illustrates spot diagrams 410-1 through 410-6 (hereinafter collectively referred to as "spot diagrams 410") in SI 130 for an SI system, according to some embodiments. Spot diagrams 410 are obtained from optical ray-tracing simulation for scattered ray cones 400 (cf. FIG. 4A) originated from different field points, and assuming a cross section of the sample interface with surfaces including tissue, window, glycerol, WMO, water, and an ideal DO lens 133. For example, spot diagrams 410-1, 410-2 and 410-3 are generated from field points at the surface of sample 135, located to the 'left,' 'center,' and 'right' (e.g., from the incidence plane formed by rays 300a and scattered light 100c). Spot diagrams 410-4, 410-5 and 410-6 are generated from field points at a depth of sample 135 (e.g., 50 µm), located to the 'left,' 'center,' and 'right.' The vertical line (B) demarcates the surface of DO 133. Spot diagrams 410 may be associated with field points at the corners of a 764 µm long field-of-view (FOV) oblique section. The circle 450 on each spot diagram 450 represents the airy disk (e.g., diffraction limit).

Accordingly, some embodiments provide a near diffraction-limited focal area for lens 310 (illustrated by circles 450 in spot diagrams 410) for all interested field points, assuming a sample refractive index of 1.45. For illustration purposes only, DO 133 may be stopped down to a NA of 0.48, which slightly oversamples the object for emission spectra arising from 660 nm and 785 nm excitable fluorophores. In object space, the expected Rayleigh resolution is 0.82 an and 0.96 an for 700 nm and 820 nm emission signal, respectively. With 17.4× magnification (cf. FIGS. 3A-B), the anticipated sensor sampling is 0.37 m. A near diffraction-limited performance for all interested field points, assuming a sample refractive index of 1.45. The lateral resolution of system 10, using fluorescent beads having a diameter of approximately 200 nm, is listed in Table 1, below. In some embodiments, the beads may be suspended in a water-glycerol-agarose gel. Mixing glycerol into the gel brings the index closer to the index of tissue, limiting the misalignment of the light sheet to the sample plane due to refraction at the tissue-window interface. For preparing Table 1, and purely for illustrative purposes, fifty beads in the left, center, and right fifth of the field of view (FOV) of a XY section are used to calculate the full-width, half-maximum (FWHM). The choice of coordinate axes for Table 1 is rotated around Y by 30° from the detection optical axis, so Dx contains contributions from both the lateral and axial point-spread functions. The FWHM of the light sheet, which may be about 9.0 µm, is measured by imaging the beam reflection off the top surface of the window.

TABLE 1

| FWHM measurements of 660 nm-excited beads in an XY section. | | |
|---|---|---|
| Region | Δx (µm) | Δy (µm) |
| Left | 1.10 ± 0.12 | 1.09 ± 0.19 |
| Center | 1.03 ± .08 | 0.85 ± 0.10 |
| Right | 1.16 ± .25 | 0.96 ± 0.13 |

Figure 5:
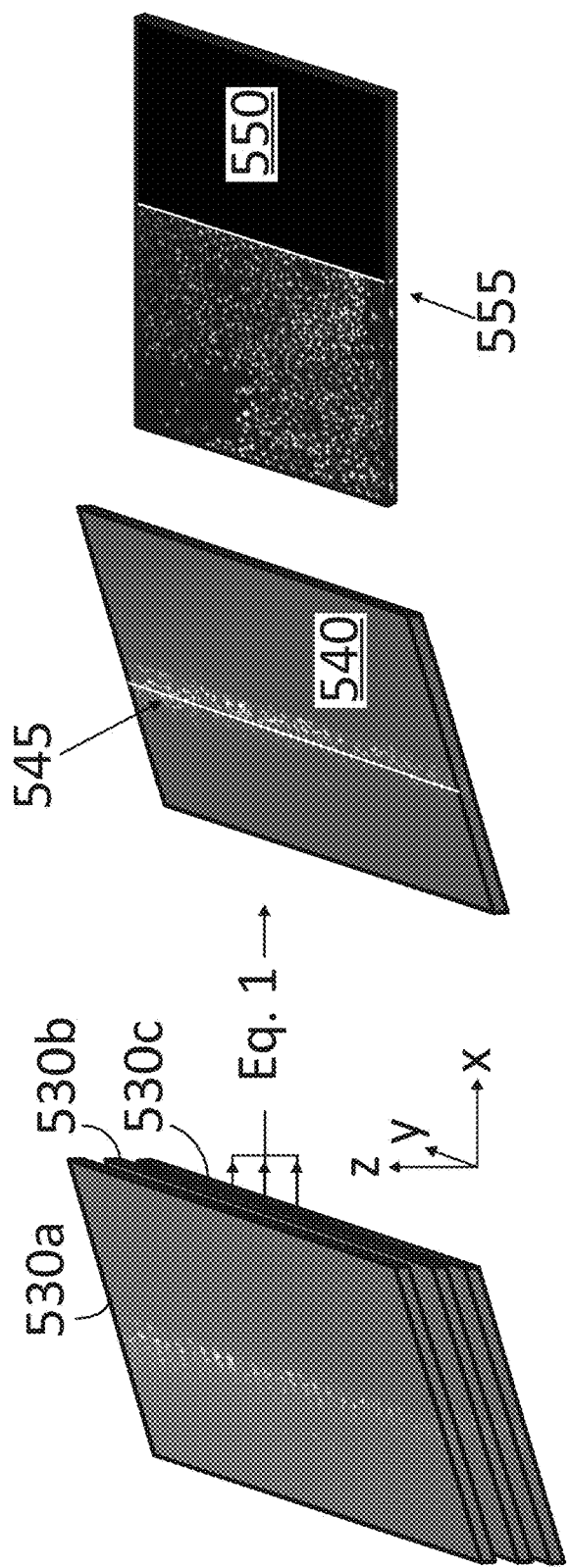
FIG. 5 illustrates a reconstruction of two-dimensional (2D) sections in an SI system, according to some embodiments.

FIG. 5 illustrates a reconstruction of two-dimensional (2D) images 530a (e.g., $I_1$, in Eq. 1), 530b (e.g., $I_2$, in Eq. 1), and 530c (e.g., $I_3$, in Eq. 1) in System 10, according to some embodiments. Scattering suppression techniques as disclosed herein may be desirable in configurations including high scattering coefficients (e.g., dense biological tissues). The imaging depth of an LSFM as disclosed herein may be increased by enhanced image contrast associated with better scattering suppression. Due to their minimal scattering, small, transparent specimens may be studied extensively with LSFM. Further, in LSFM systems as disclosed herein, more dense tissues may be efficiently imaged through reduced scattering. Accordingly, embodiments as disclosed herein enable tissue imaging without performing cumbersome optical clearing techniques which change the cellular composition to a more homogeneous index (e.g., to reduce scattering effects) or alter the scattering structures themselves. Various tissue-clearing methods have been applied to LSFM, but in each case the tissue is effectively fixed, preventing observation of live cultures. Other approaches to background reduction in LSFM include line scanned confocal microscopy, which use physical or virtual slits to eliminate out of focus light in one dimension to boost contrast. While contrast is increased in some embodiments, some embodiments of an SI system as disclosed herein can be configured to reject scattered and out-of-focus in both dimensions, further lowering the background floor.

Images $I_1$ (530a), $I_2$ (530b), and $I_3$ (530c) are collected with phase-shifted SI patterns (cf. Eq. 1) and used to reconstruct $I_{SI}$, (540) via Eq. 1. A horizontal line 545 in $I_{SI}$ 540 corresponding to the sample depth of interest is used to reconstruct a line 555 of $I_{XY}$ 550. Note that the plane of $I_{SI}$ may be oblique relative to the XY plane of sample interface 130 (cf., axes XYZ consistent with FIGS. 3A and 4A). Accordingly, $I_{SI}$ and $I_{XY}$ may intersect along a single line 555 for each line of image $I_{XY}$ 550. In some embodiments, line 555 may coincide, approximately, with a pixel row in sensor 150 (cf. FIGS. 1A-B). By stacking multiple planes $I_{SI}$ 540 together, each of the camera pixel rows 555 may be obtained to form an XY view of sample 135. Furthermore, in some embodiments a 3D image of sample 135 (cf. FIGS. 1A-B) may be obtained by stitching together multiple planes 540 stacked along the X-direction.

Figure 6:
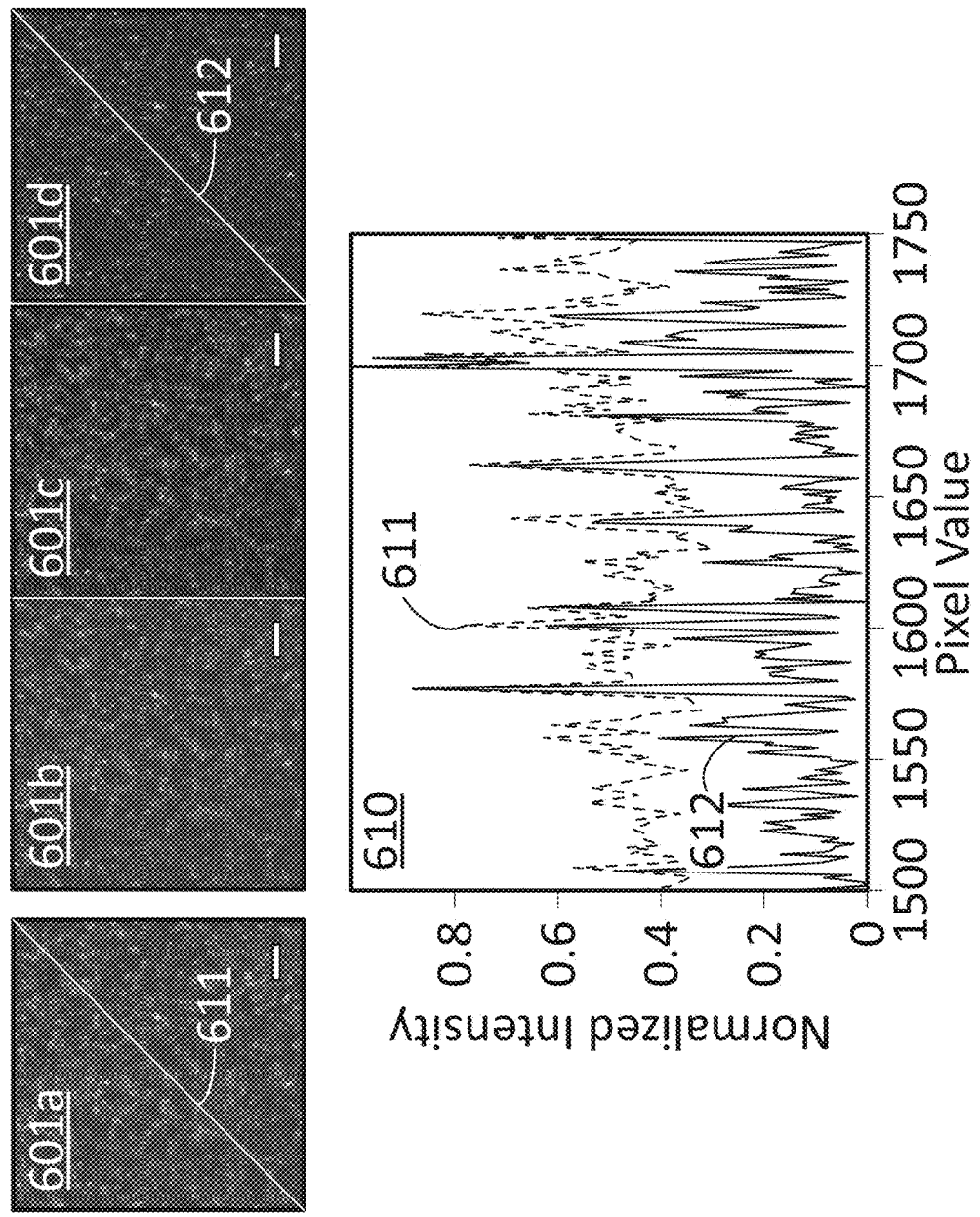
FIG. 6 illustrates a sample image including efficient removal of high fluorescent background in an SI system, according to some embodiments.

FIG. 6 illustrates sample images 601a, 601b, 601c, and 601d (hereinafter, collectively referred to as images 601). Accordingly, images 601b, 601c and 601d include efficient removal of high fluorescent background in an SI system. Images 601 include a 512×512 pixel, XY reconstructions 50 µm into agarose gel containing high concentrations of beads. The scale bar is 10 µm. More specifically, image 601a illustrates a sum image, which would be the imaging result obtained without scattering suppression. Images 601b-d include image reconstructions with imaging field pattern periods of 35, 11, and 3.7 µm/cycle, respectively. Accordingly, the spatial frequency of images 601b-d are adjusted by actuating spatial frequency modulator 120 (e.g., by displacing prism 202 towards prism 201, cf. FIG. 2A).

Image 610 illustrates the significant background reduction between cross section 611 corresponding to image 601a (no structured illumination) and cross-section 612 corresponding to image 601d (structured illumination with a high spatial frequency 3.7 µm). The image samples were collected using high concentrations of 200 nm beads in the tissue samples. The finest spatial frequency in image 601d reduces background scattering by nearly an order of magnitude as compared to the sum illumination in image 601a. The improved performance with finer patterns is due to both the removal of scattering from smaller structures and the subtraction of the out-of-focus component of the light sheet.

Figure 7:
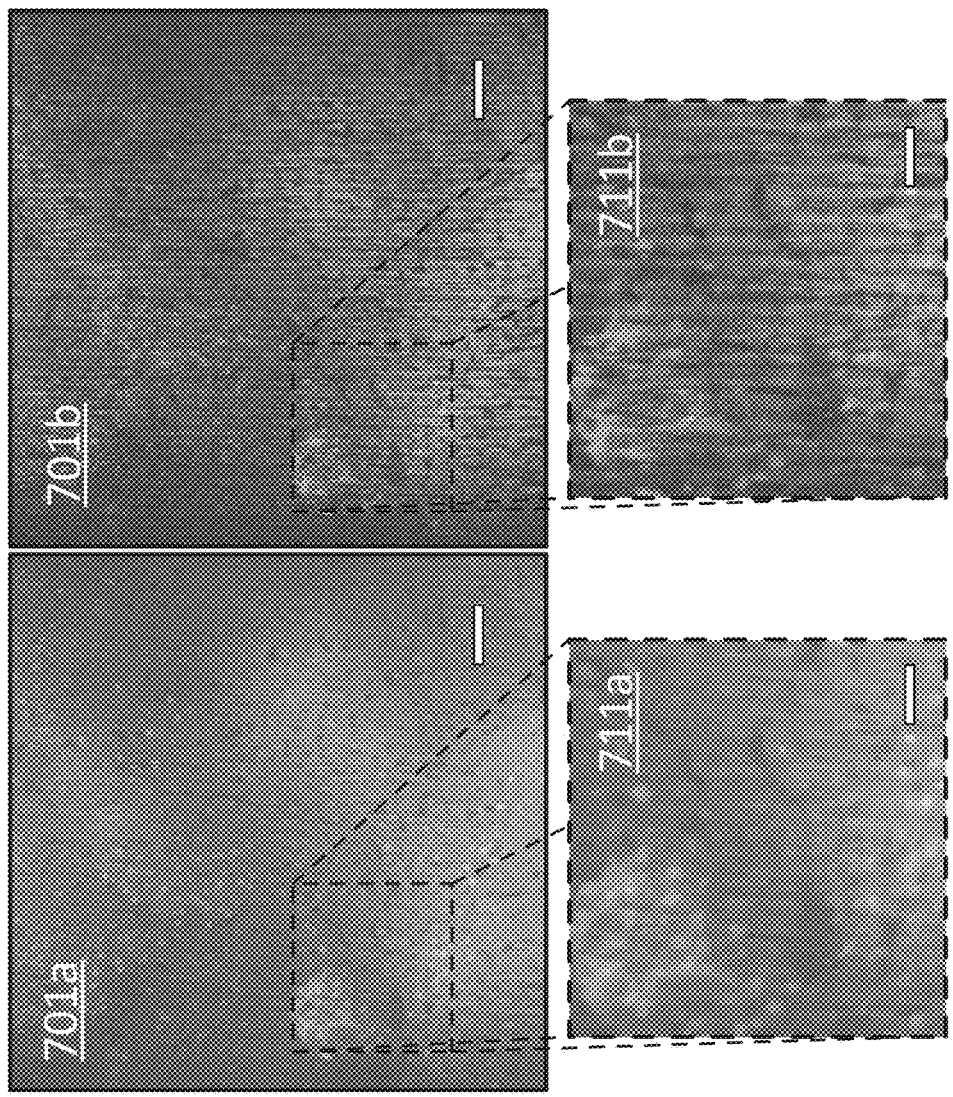
FIG. 7 illustrates a removal of high fluorescent background in an SI system for a tissue sample, according to some embodiments.

FIG. 7 illustrates a removal of high fluorescent background in an SI system for a tissue sample, according to some embodiments. For exemplary purposes only, and without limitation, the tissue sample may be a large excision of mouse liver tissue stained with DRAQ5™ and IR783. DRAQ5™ is excited at 660 nm (e.g., illumination wavelength) and localizes nuclear features, while the IR783 is excited at 785 nm (e.g., illumination wavelength) and stains for general tissue morphology. Without limitation, and for illustrative purposes only, FIG. 7 shows an XY reconstruction of the mouse liver tissue at a depth of 31 µm. Image 701a includes a sum image (e.g., no SI scattering removal). Image 701b is an image obtained with an SI system for removing scattering interference. The scale bars are 80 µm for images 701a-b, and 25 µm for insets (image 711a and 711b, respectively).

In image 701b the XY scan was collected using an imaging field 100b with a spatial period of 11 µm/cycle (e.g., a spatial frequency of 1/11 cycles per µm). The lines in the scan are read by the camera at 1,000 frames per second (fps). Given the system magnification of approximately 18×, the total time to image a 1 mm$^2$ area is approximately 8 seconds per channel, wherein each channel may correspond to a different illumination wavelength. The set of SLM states are unchanged for 660 nm illumination wavelength and for 785 nm illumination wavelengths, making it possible to image both channels simultaneously. Accordingly, system 10 as disclosed herein maintains high resolution and contrast, despite the oblique nature of the light sheet and the presence of scattered light in the sample. The incorporation of a WMO enables examination of sub-cellular features while simultaneously creating an inverted configuration, while SI limits the extent to which these features are obscured by background. Applications of these techniques may be particularly useful in pathology departments, where tissues need to be sectioned rapidly, and in research settings, where volumetric imaging of cells in experiments may require continuous monitoring.

Figure 8:
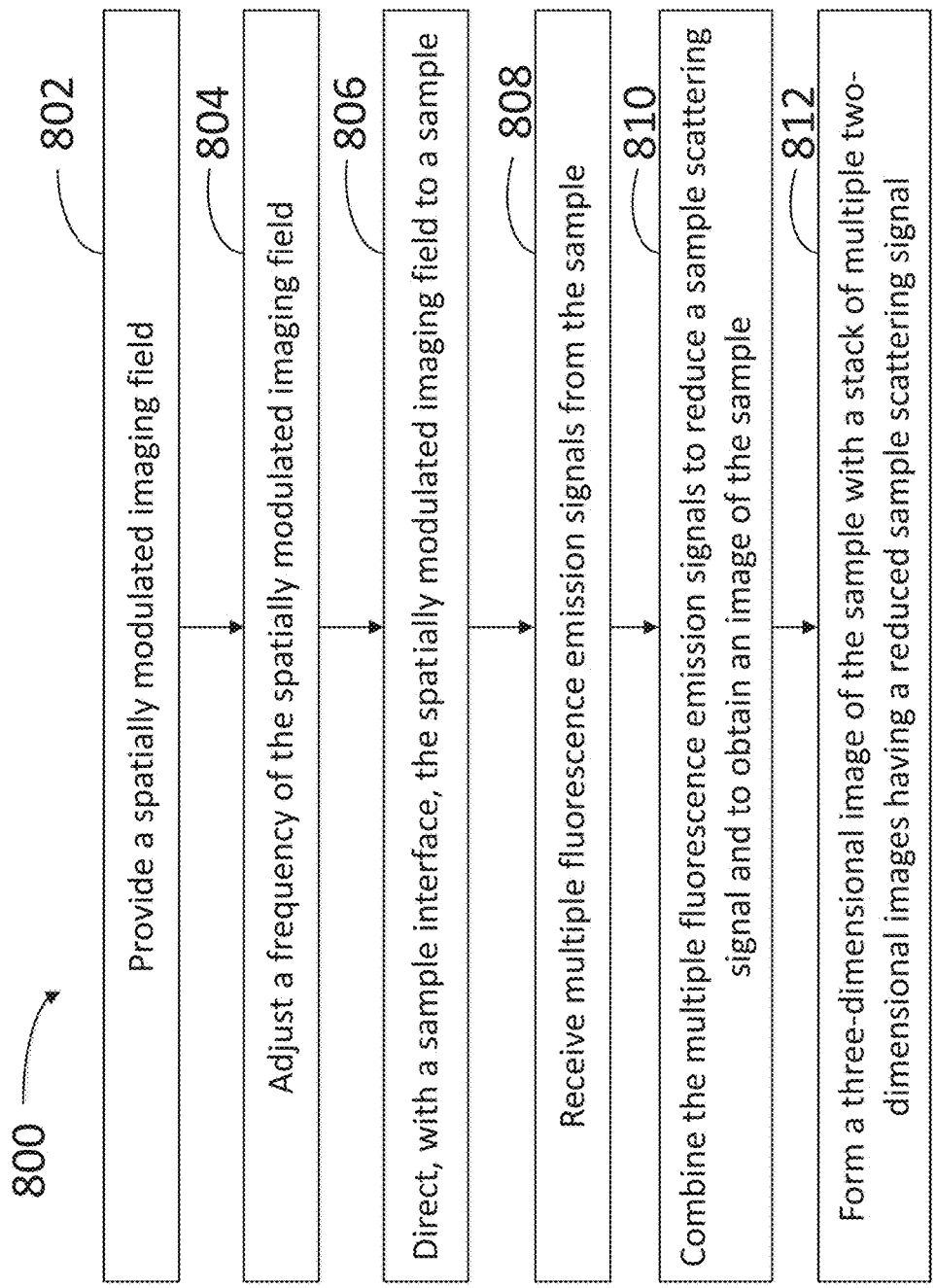
FIG. 8 illustrates steps in a flow chart for a method of forming an image of a sample, according to some embodiments.

FIG. 8 illustrates steps in a flow chart for a method 800 of forming an image of a sample, according to some embodiments. Method 800 may be performed at least partially by any one of the components in a system for inverted light sheet microscopy, such as an SI stage, a spatial frequency modulation stage, and a sample interface stage, as disclosed herein (e.g., SI system 10 including SI stage 110, spatial frequency modulation stage 120, and sample interface 130), while collecting one or more images from a sample. At least some of the steps in method 800 may be performed by a computer having a processor executing commands stored in a memory of the computer (e.g., memory 40 and processor 30). Further, steps as disclosed in method 800 may include retrieving, editing, and/or storing files in a database that is part of, or is communicably coupled to, the memory of the computer. Methods consistent with the present disclosure may include at least some, but not all, of the steps illustrated in method 800, performed in a different sequence. Furthermore, methods consistent with the present disclosure may include at least two or more steps as in method 800 performed overlapping in time, or almost simultaneously.

Step 802 includes providing a spatially modulated imaging field. In some embodiments, step 802 may include selecting the first two diffraction order beams (±1) from an SLM with a double slit. Further, in some embodiments step 802 includes selecting a spatial phase for the spatially modulated imaging field by configuring of the pixels in the SLM corresponding to a square wave having a selected phase. Moreover, in some embodiments step 802 includes providing multiple spatially modulated imaging fields, each imaging field having a spatial phase shift that accrues to a 2π phase shift over the multiple spatially modulated imaging fields.

Step 804 includes adjusting a frequency of the spatially modulated imaging field. In some embodiments, step 804 includes linearly displacing an optical element to interfere two optical beams at a selected angle.

Step 806 includes directing, with a sample interface, the spatially modulated imaging field to a sample. In some embodiments, step 806 includes moving the sample along a plane oblique to a plane including the spatially modulated light, and obtaining a plurality of images of the sample to form a three-dimensional image of the sample.

Step 808 includes receiving multiple fluorescence emission signals from the sample. In some embodiments, step 808 includes receiving a first fluorescence emission signal from a structured illumination field having a spatial frequency and a first phase, receiving a second fluorescence emission signal having the spatial frequency with a second phase, and receiving a third fluorescence emission signal having the spatial frequency with a third phase. In some embodiments, step 808 includes receiving the plurality of fluorescence emission signals along a line intersecting a plane including the spatially modulated imaging field and a plane of motion of the sample. In some embodiments, step 808 includes receiving a first fluorescence signal with the spatially modulated imaging field having a first phase, receiving a second fluorescence signal with the spatially modulated imaging field having a second phase, and receiving a third fluorescence emission signal with the spatially modulated imaging field having a third phase.

Step 810 includes combining the multiple fluorescence emission signals to reduce a sample scattering signal and to obtain an image of the sample.

Step 812 includes forming a three-dimensional image of the sample with a stack of multiple two-dimensional images having a reduced sample scattering signal. In some embodiments, step 812 includes displacing the sample in an XY stage of the sample interface along one direction (e.g., the X-direction), and collecting a two-dimensional image having a reduced sample scattering signal for each of multiple positions of the XY stage.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C, any combination of A, B, and C, and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The invention claimed is:

1. A system, comprising:
   a structured illumination stage to provide a spatially modulated imaging field;
   a spatial frequency modulation stage to adjust a frequency of the spatially modulated imaging field;
   a sample interface stage to direct the spatially modulated imaging field to a sample;
   a sensor configured to receive a plurality of fluorescence emission signals from the sample; and
   a processor configured to reduce a sample scattering signal and to provide a fluorescence emission signal from a portion of the sample including the spatially modulated imaging field.

2. The system of claim 1, wherein the structured illumination stage comprises an anamorphic optical component to form the spatially modulated imaging field in a sheet of light.

3. The system of claim 1, further comprising a phase shifting stage to adjust the phase of the spatially modulated imaging field, the structured illumination stage comprising a spatial light modulator configured to spatially separate two diffracted beams having a selected phase shift between them, to form the spatially modulated imaging field.

4. The system of claim 1, wherein the spatial frequency modulation stage comprises a movable optical element configured to adjust an angle of incidence formed between a first diffracted illumination beam and a second diffracted illumination beam provided by the structured illumination stage, thereby to adjust a spatial frequency of an interference pattern between the first diffracted illumination beam and the second diffracted illumination beam.

5. A method for forming an image of a sample, comprising:
   providing a spatially modulated imaging field;
   adjusting a frequency of the spatially modulated imaging field;
   directing, with a sample interface, the spatially modulated imaging field to a sample;
   receiving a plurality of fluorescence emission signals from the sample; and
   combining the plurality of fluorescence emission signals to reduce a sample scattering signal and to obtain an image of the sample.

6. The method of claim 5, wherein receiving a plurality of fluorescence emission signals from the sample comprises receiving a first fluorescence emission signal from a structured illumination field having a spatial frequency and a first phase, receiving a second fluorescence emission signal having the spatial frequency with a second phase, and receiving a third fluorescence emission signal having the spatial frequency with a third phase.

7. The method of claim 5, wherein receiving a plurality of fluorescence emission signals comprises receiving the plurality of fluorescence emission signals along a line intersecting a plane including the spatially modulated imaging field and a plane of motion of the sample.

8. The method of claim 5, further comprising moving the sample along a plane oblique to a plane including the spatially modulated imaging field, and obtaining a plurality of images of the sample to form a three-dimensional image of the sample.

9. The method of claim 5, wherein adjusting a frequency of the spatially modulated imaging field comprises linearly displacing an optical element to interfere two optical beams at a selected angle.

10. The method of claim 5, wherein receiving a plurality of fluorescence emission signals from the sample comprises receiving a first fluorescence signal with the spatially modulated imaging field having a first phase, receiving a second fluorescence signal with the spatially modulated imaging field having a second phase, and receiving a third fluorescence emission signal with the spatially modulated imaging field having a third phase.

* * * * *

UNITED STATES PATENT AND TRADEMARK OFFICE
CERTIFICATE OF CORRECTION

PATENT NO.        : 10,401,605 B2
APPLICATION NO.   : 15/843692
DATED             : September 3, 2019
INVENTOR(S)       : Joseph R. Landry et al.

It is certified that error appears in the above-identified patent and that said Letters Patent is hereby corrected as shown below:

On the Title Page

Item (73), Line 1, should read:
-- SCREEN HOLDINGS CO., LTD. --

Signed and Sealed this
Fifth Day of November, 2019

Andrei Iancu
*Director of the United States Patent and Trademark Office*